United States Patent
Witcher et al.

(10) Patent No.: US 10,123,750 B2
(45) Date of Patent: Nov. 13, 2018

(54) METHODS AND DEVICES FOR PREDICTING AND/OR DETECTING SEIZURES

(71) Applicant: Wake Forest University Health Sciences, Winston-Salem, NC (US)

(72) Inventors: Mark R. Witcher, Winston-Salem, NC (US); Robert E. Hampson, Kernersville, NC (US); Sam Deadwyler, Winston-Salem, NC (US); Daniel E. Couture, Winston-Salem, NC (US); Gautam Popli, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 488 days.

(21) Appl. No.: 14/759,092

(22) PCT Filed: Jan. 3, 2014

(86) PCT No.: PCT/US2014/010159
§ 371 (c)(1),
(2) Date: Jul. 2, 2015

(87) PCT Pub. No.: WO2014/107564
PCT Pub. Date: Jul. 10, 2014

(65) Prior Publication Data
US 2015/0335294 A1   Nov. 26, 2015

Related U.S. Application Data

(60) Provisional application No. 61/748,510, filed on Jan. 3, 2013.

(51) Int. Cl.
*A61B 5/04* (2006.01)
*A61B 5/00* (2006.01)
(Continued)

(52) U.S. Cl.
CPC .......... *A61B 5/7275* (2013.01); *A61B 5/0476* (2013.01); *A61B 5/4094* (2013.01);
(Continued)

(58) Field of Classification Search
CPC ........................... A61B 5/4076; A61B 5/4094
See application file for complete search history.

(56) References Cited

U.S. PATENT DOCUMENTS

| | | | |
|---|---|---|---|
| 2003/0135128 A1* | 7/2003 | Suffin | A61B 5/0006 600/544 |
| 2006/0111644 A1* | 5/2006 | Guttag | A61B 5/048 600/544 |
| 2007/0067003 A1* | 3/2007 | Sanchez | A61N 1/36082 607/45 |

FOREIGN PATENT DOCUMENTS

WO    WO 2012/167140 A1    12/2012

OTHER PUBLICATIONS

International Preliminary Report on Patentability corresponding to International Patent Application No. PCT/US2014/010159 (8 pages) (dated Jul. 7, 2015).

(Continued)

*Primary Examiner* — Christian Jang
(74) *Attorney, Agent, or Firm* — Myers Bigel, P.A.

(57) ABSTRACT

The present invention provides methods and devices for predicting, preventing, detecting and/or treating seizures. In some embodiments, the present invention provides methods/devices for predicting a seizure prior to its inception, wherein the seizure is predicted based upon neuronal activity in the CA3 region of a patient's hippocampus.

28 Claims, 2 Drawing Sheets

(51) Int. Cl.
    *A61B 5/0476*    (2006.01)
    *A61N 1/05*       (2006.01)
    *A61N 1/36*       (2006.01)

(52) U.S. Cl.
    CPC ....... *A61N 1/0529* (2013.01); *A61N 1/36025* (2013.01); *A61N 1/36064* (2013.01)

(56) References Cited

OTHER PUBLICATIONS

International Search Report and Written Opinion for PCT/US2014/010159 dated Apr. 25, 2014.

\* cited by examiner

Figure 2

METHODS AND DEVICES FOR PREDICTING AND/OR DETECTING SEIZURES

RELATED APPLICATIONS

The present application is a 35 U.S.C. § 371 national phase application of PCT International Application No. PCT/US2014/010159, filed Jan. 3, 2014, which claims priority from U.S. Provisional Patent Application No. 61/748,510, filed Jan. 3, 2013; the disclosures of which are hereby incorporated herein by reference in their entirety. PCT International Application No. PCT/US2014/010159 is published in English as PCT Publication No. WO 2014/107564.

FIELD OF THE INVENTION

The present invention concerns apparatuses and associated methods useful for predicting, preventing, detecting and/or treating seizures.

BACKGROUND

Epilepsy is a common chronic neurologic disorder which causes recurrent seizures and affects 0.5 to 1 percent of the population (Hauser et al., EPILEPSIA 34:453 (1993)). Seizures occur when there is an imbalance in the electrical activity of the brain. The abnormality may be in a small area of the brain or may involve the entire brain. Epilepsy can be congenital or can also be caused by head injury, birth trauma, infections, brain tumor, hemorrhage, or stroke. Diagnosis of epilepsy requires multi-modality testing, often in multiple phases. Initially, clinical exam and patient history are of primary importance for diagnosis. Other tests may include magnetic resonance imaging (MRI) to examine for structural abnormalities, single photon emission computed tomography (SPECT or positron emission tomography (PET) to examine for functional abnormality, electroencephalography (EEG) to record electrical impulses of the brain and their foci, magnetoencephalography (MEG) to co-localize electrical foci with structural abnormalities, and blood tests to exclude other diseases.

In spite of optimal medical management, more than one-third of all epilepsy patients have incompletely controlled seizures or debilitating medication side effects (Kwan and Brodie, N. ENGL. J. MED. 342:314 (2000); Sander, EPILEPSIA 34:1007 (1993); Sillanpaa and Schmidt, EPILEPSY BEHAV. 8:713 (2006)). Medically refractory epilepsy is associated with excess injury and mortality, psychosocial dysfunction, and significant cognitive impairment. Resective or disconnective surgery is associated with long term seizure freedom in 60-80% of patients (Engel, Jr. et al., EPILEPSIA 44:741 (2003); Engel, Jr. et al., NEUROL. 60:538 (2003); Lee et al., ANN. NEUROL. 58:525 (2005)). Surgery for patients whose epilepsy has proven refractory to anti-epileptic drugs (AEDs) provides a high likelihood, of reduction in seizure frequency, is generally safe, and is recommended for selected patients with refractory partial seizures.

In order to appropriately diagnose epilepsy for possible surgical intervention, it is generally necessary to conduct an inpatient workup, referred to as Phase I monitoring. The primary goal of this analysis is to confirm the diagnosis of epilepsy and requires simultaneous video and electroencephalographic (EEG) monitoring, 24 hours a day in an epilepsy monitoring unit (EMU), which enables correlation of complete clinical behavior, with seizure information from the EEG. Through Phase I monitoring, the part of the brain responsible for seizure activity can often be localized. However, if data collected during the Phase I admission does not provide enough information to localize the seizure focus, then invasive, inpatient, Phase II monitoring may be needed. This standard approach involves surgery to place cortical electrodes and depth electrodes directly into the brain. Cortical electrodes consist of parallel rows of electrode contacts placed directly on the cortical surface of the brain. Depth electrodes are inserted into the brain to reach deep recording sites, often in the hippocampus and amygdala. These electrodes are placed to provide more accurate information as to the location of epileptic focus and to correlate with continuous video monitoring. After recovery from surgery, implanted electrodes are connected to monitoring equipment which can detect seizure activity and localize seizure foci. In order to provoke seizures, anti-epileptic medications are often weaned or discontinued.

The Hippocampus in Seizure Generation

Mesial temporal lobe epilepsy (MTLE) is a common form of medically-refractory epilepsy which is characterized by spontaneous and progressive seizures. Mesial structures include the amygdala, the uncus, the hippocampus, and the parahippocampal gyrus. While in many patients it can be associated with past hippocampal injury followed by a latency period of 5-10 years, other cases are idiopathic. Characteristic changes are well described in the hippocampus of MTLE patients, including structural changes of sclerosis and gliosis, predictable neuronal loss in particular hippocampal subfields and molecular changes leading to hyperexcitability, as recently reviewed (O'Dell et al., J. NEUROSCI. RES. 90:913 (2012)). Diagnosis of MTLE conventionally requires the multi-modal approach described above to define the hippocampus as a seizure generator. The depth electrodes conventionally placed are composed of a series of macrocontact electrodes which are designed to detect a narrow frequency bandwidth (0.1-100 Hz) of neuronal field potential changes from a large surface area of the brain with a wide inter-electrode spacing (5-10 mm apart) (Worrell et al., BRAIN 131:928 (2008)).

The Use of High Frequency Oscillations and Spatiotemporal Correlation for the Detection of Seizures While the conventional, slow frequency range is useful for the detection of seizures, it neglects higher frequency ranges and more specific, single neurons which are likely useful in the early detection of seizure activity (Truccolo et al., NATURE NEUROSCI. 14:635 (2011)). High-frequency oscillations (HFO) have been described including ranges of 80-250 Hz, >250-500 Hz (Bragin et al., J. NEUROSCI. 22:2012 (2002); Bragin et al., ANN. NEUROL. 52:407 (2002); Worrell et al., BRAIN 131:928 (2008)) and even higher (up to 10 K Hz) (Bower et al., 2012). Higher frequency oscillations are thought to be unique to the pathologic hippocampus as they have been identified primarily in the epileptic kainate rodent model (Bragin et al., EPILEPSIA 40:127 (1999)) and the epileptic human mesial temporal lobe (Bragin et al., EPILEPSIA 40:127 (1999); Bragin et al., ANN. NEUROL. 52:407 (2002)). Reliable detection of these HFOs are optimized from implanted microelectrodes using supra-standard filtration (Bower et al., EPILEPSIA 53:807 (2012); William, J. NEURONAL ENG. 9:056007 (2012); Worrell et al., BRAIN 133:928 (2008)). Simultaneous recording from macro/micro electrodes indicate that HFOs are increased in seizure generating zones of the human mesial temporal lobe prior to or at the onset of seizures, and that the presence of these electrographic signals may be more sensitive than structural changes typically relied upon for hippocampal involvement in seizure generation (Worrell et al., BRAIN 131:928 (2008)). Supporting these findings, a cat model of seizures shows that ripple-frequency HFOs are strongly associated with seizure onset, and evidence suggests that they may play a fundamental role in recruiting surrounding neuronal tissue into seizing, thus creating a. pathological summation effect of seizure propagation (Grenier et al., J. NEUROPHYSIOL. 86:1884 (2001)).

Hippocampal Subfield Anatomy

In brief, the anatomical hippocampus is subdivided into subfields known as the CA1-CA4 regions, each populated by a stereotypical cytoarchitecture with predictable synaptic interconnections between subfields (DUVERNOY, THE HUMAN HIPPOCAMPUS: FUNCTIONAL ANATOMY, VASCULARIZATION AND SERIAL SECTIONS WITH MRI (2005)). Importantly, the subfield of CA3 gives putative monosynaptic input to the CA1 subfield via a collection of pyramidal neuronal axons known as the Schaffer collateral system (Schaffer, ARCH. MIKROSKOP. ANATOMIE 39:611 (1892)); the CA1 subfield subsequently serves in the main output pathway of the hippocampal formation. In the past several years, much attention has focused on how the firing pattern of CA3 neuronal population influences the neuronal discharge of the CA1 subfield (Guzowski et al., NEURON 44:581 (2004)) leading recently to the development of verified animal models which reliably predict multineuronal ensemble firing patterns of CA1 based on the recorded discharge patterns of CA3 (Berger et al., J. NEURONAL ENG. 8:046017 (2011); Hampson et al., IEEE TRANSACTIONS 20:184 (2012)).

Recording of these hippocampal ensembles for use in functional predictions of seizures can now be readily adapted to human application using FDA-approved materials within a well-defined clinical application.

Hippocampal Recording and Development of Neuronal Ensemble Models from Animal Studies As described above, the hippocampus has a stereotypical cytoarchitecture which includes a putative monosynaptic connection between subfields (DUVERNOY, THE HUMAN HIPPOCAMPUS: FUNCTIONAL ANATOMY, VASCULARIZATION AND SERIAL SECTIONS WITH MRI (2005)). The neuronal output of CA3 has recently been shown in mathematical models of animal hippocampus to influence the neuronal activity pattern of CA1 neurons, forming a neuronal ensemble. In the rodent hippocampus, one such operational nonlinear systems model characterized the neuronal activity of CA1 utilizing individualized or generic inputs derived from CA3 neurons, recorded while the animals underwent cognitive behavioral testing (Berger et al., J. NEURONAL ENG. 8:046017 (2011); Hampson et al., IEEE TRANSACTIONS 20:184 (2012); Zanos et al., IEEE TRANSACTIONS 16:336 (2008)). Development of this model has been shown to allow reliable recording of CA3 neuronal discharges with subsequent accurate prediction of the activity or CA1 postsynaptic cells via the Schaffer collateral system (Berger et al., J. NEURONAL ENG. 8:046017 (2011)).

SUMMARY OF THE INVENTION

A first aspect of the invention is a method of predicting and/or detecting a seizure. In some embodiments, the method comprises, consists essentially of or consists of detecting neuronal activity in the CA3 region of a patient's hippocampus and analyzing the detected neuronal activity to predict and/or detect a seizure. In some embodiments, the method comprises, consists essentially of or consists of detecting neuronal activity in the CA3 region of a patient's hippocampus and in at least one alternate region of the patient's brain (e.g., the Schaffer collateral and/or CA1 regions of the patient's hippocampus, the subiculum and/or the entorhinal cortex) and analyzing the detected neuronal activity to predict and/or detect a seizure. In some embodiments, analyzing the detected neuronal activity comprises using of an algorithm to predict future neuronal activity.

A second aspect of the present invention is a method of inhibiting and/or preventing the propagation of a seizure. In some embodiments, the method comprises, consists essentially of or consists of predicting and/or detecting a seizure in a patient and delivering a one or more stimuli to the patient's brain to inhibit and/or prevent the propagation of the seizure. In some embodiments, the seizure is predicted and/or detected using a method/device of the present invention. In some embodiments, propagation of the seizure is inhibited and/or prevented by stimulating the CA3 region of the patient's hippocampus, the Schaffer collateral region of the patient's hippocampus, the CA1 region of the patient's hippocampus, the CA2 region of the patient's hippocampus, the patient's perforant pathway, the patient's subiculum, the patient's entorhinal cortex and/or the patient's temporal cortex (with an electrical stimulus delivered by one or more electrodes, for example).

A third aspect of the present invention is a device useful for predicting and/or detecting a seizure. In some embodiments, the device comprises, consists essentially of or consists of a controller operatively connected to one or more electrodes (e.g., one or more single-unit neuron detectors and/or one or more multi-unit neuron detectors), wherein at least one of electrodes is configured to detect neuronal activity in the CA3 region of a patient's hippocampus and wherein the controller is configured to predict and/or detect a seizure based upon neuronal activity detected in the CA3 region of the patient's hippocampus and/or a connected region of the brain. In some embodiments, the device comprises, consists essentially of or consists of a controller operatively connected to a plurality of electrodes (e.g., single-unit neuron detectors and/or multi-unit neuron detectors), wherein one or more of the electrodes is configured to detect neuronal activity in the CA3 region of a patient's hippocampus and one or more of the electrodes is configured to detect neuronal activity in an alternate region of the patient's brain (e.g., the Schaffer collateral and/or CA1 regions of the patient's hippocampus, the subiculum and/or the entorhinal cortex) and wherein the controller is configured to predict and/or detect a seizure based upon neuronal activity detected in the CA3 region of the patient's hippocampus and the alternate region of the patient's brain. In some embodiments, the controller is configured to predict and/or detect a seizure using an algorithm that predicts future neuronal activity based upon the detected neuronal activity.

A fourth aspect of the present invention is a device useful for inhibiting and/or preventing the propagation of a seizure. In some embodiments, the device comprises, consists essentially of or consists of a controller operatively connected to one or more electrodes (e.g., one or more single-unit neuron detectors and/or one or more multi-unit neuron detectors), wherein at least one of electrodes is configured to detect neuronal activity in the CA3 region of a patient's hippocampus, wherein at least one of the electrodes is configured to deliver an electrical stimulus to the CA3 region of the patient's hippocampus, wherein the controller is configured to predict and/or detect a seizure based upon neuronal activity detected in the CA3 region of the patient's hippocampus and, responsive to predicting and/or detecting the seizure, to activate one more of the electrodes configured to deliver an electrical stimulus to the CA3 region of the patient's hippocampus such that one or more electrical stimuli are delivered to the CA3 region of the patient's hippocampus. In some embodiments, the device comprises, consists essentially of or consists of a controller operatively connected to one or more electrodes (e.g., one or more single-unit neuron detectors and/or one or more multi-unit neuron detectors), wherein at least one of electrodes is configured to detect neuronal activity in the CA1 region of a patient's hippocampus, wherein at least one of the electrodes is configured to deliver an electrical stimulus to the CA1 region of the patient's hippocampus, wherein the controller is configured to predict and/or detect a seizure based upon neuronal activity detected in the CA1 region of the patient's hippocampus and, responsive to predicting and/or detecting the seizure, to activate one more of the electrodes configured to deliver an electrical stimulus to the CA1 region of the patient's hippocampus such that one or more electrical stimuli are delivered to the CA1 region of the patient's hippocampus. In some embodiments, the device comprises, consists essentially of or consists of a controller operatively connected to one or more electrodes (e.g., one or more single-unit neuron detectors and/or one or more multi-unit neuron detectors), wherein one or more of the electrodes is configured to detect neuronal activity in the CA3 region of a patient's hippocampus and one or more of the electrodes is configured to detect neuronal activity in an alternate region of the patient's brain (e.g., the Schaffer collateral and/or CA1 regions of the patient's hippocampus, the subiculum and/or the entorhinal cortex), wherein one or more of the electrodes is configured to deliver an electrical stimulus to the CA3 region of the patient's hippocampus and/or one or more of the electrodes is configured to deliver an electrical stimulus to an alternate region of the patient's brain (e.g., the Schaffer collateral and/or CA1 regions of the patient's hippocampus, the subiculum and/or the entorhinal cortex), wherein the controller is configured to predict and/or detect a seizure based upon neuronal activity detected in the CA3 region of the patient's hippocampus and the alternate region of the patient's brain and, responsive to predicting and/or detecting the seizure, to activate one more of the electrodes configured to deliver an electrical stimulus to the CA3 region of the patient's hippocampus and/or one or more of the electrodes configured to deliver an electrical stimulus to the alternate region of the patient's brain such that one or more electrical stimuli are delivered to the CA3 region of the patient's hippocampus and/or one or more electrical stimuli are delivered to the alternate region of the patient's brain. In some embodiments, the device comprises, consists essentially of or consists of a controller operatively connected to one or more electrodes (e.g., one or more single-unit neuron detectors and/or one or more multi-unit neuron detectors), wherein one or more of the electrodes is configured to detect neuronal activity in the CA1 region of a patient's hippocampus and one or more of the electrodes is configured to detect neuronal activity in an alternate region of the patient's brain (e.g., the Schaffer collateral and/or CA3 regions of the patient's hippocampus, the subiculum and/or the entorhinal cortex), wherein one or more of the electrodes is configured to deliver an electrical stimulus to the CA1 region of the patient's hippocampus and/or one or more of the electrodes is configured to deliver an electrical stimulus to an alternate region of the patient's brain (e.g., the Schaffer collateral and/or CA3 regions of the patient's hippocampus, the subiculum and/or the entorhinal cortex), wherein the controller is configured to predict and/or detect a seizure based upon neuronal activity detected in the CA1 region of the patient's hippocampus and the alternate region of the patient's brain and, responsive to predicting and/or detecting the seizure, to activate one more of the electrodes configured to deliver an electrical stimulus to the CA1 region of the patient's hippocampus and/or one or more of the electrodes configured to deliver an electrical stimulus to the alternate region of the patient's brain such that one or more electrical stimuli are delivered to the CA1 region of the patient's hippocampus and/or one or more electrical stimuli are delivered to the alternate region of the patient's brain in some embodiments, the controller is configured to predict and/or detect a seizure using of an algorithm that predicts future neuronal activity based upon the detected neuronal activity.

The foregoing and other objects and aspects of the present invention are explained in greater detail in the drawings herein and the specification set forth below. All patent references cited herein are specifically intended to be incorporated herein by reference in their entirety.

DETAILED DESCRIPTION

The present invention is explained in greater detail below. This description is not intended to be a detailed catalog of all the different ways in which the invention may be implemented or of all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention, and not to exhaustively specify all permutations, combinations and variations thereof.

It will be understood that when an element or layer is referred to as being "on", "attached to", "connected to", "coupled to", "coupled with" or "contacting" another element or layer, it can be directly on connected or coupled to the other element or layer or intervening elements or layers may be present. In contrast, when an element is referred to as being "directly on," "directly connected to" or "directly coupled to" another element or layer, there are no intervening elements or layers present. It will also be appreciated by those of skill in the art that references to a structure or feature that is disposed "adjacent" another structure or feature may have portions that overlap or underlie the adjacent structure or feature.

The present invention is described below with reference to block diagrams and/or flowchart illustrations of methods, systems and/or computer program products according to embodiments of the invention.

It is understood that various blocks of the block diagrams and/or flowchart illustrations, and combinations of blocks in the block diagrams and/or flowchart illustrations, can be implemented by computer program instructions. These computer program instructions may be provided to a processor of a general purpose computer, special purpose computer and/or other programmable data processing apparatus to produce a machine, such that the instructions, which execute via the processor of the computer or other programmable data processing apparatus, create means for implementing the functions/acts specified in the block diagrams and/or flowchart illustrations. The computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagram and/or flowchart illustrations. The computer program instructions may also be loaded onto a computer or other programmable data processing apparatus to cause a series of operational steps to be performed on the computer or other programmable data processing apparatus to produce a computer-implemented process such that the instructions which execute on the computer or other programmable data processing apparatus provide steps for implementing the functions/acts specified in the block diagrams and/or flowchart illustrations.

Accordingly, the present invention may be embodied in hardware and/or software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system. In the context of this document, a computer usable or computer-readable non-transient storage medium may be any medium that can contain and/or store the program for use by or in connection with the instruction execution system, apparatus or device. For example, the computer-usable or computer-readable medium may be an electronic, optical, electromagnetic, infrared or semiconductor system, apparatus or device.

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

As used herein, the singular forms "a", "an" and "the" are intended to include the plural forms as well, unless the context clearly indicates otherwise.

As used herein, the term "adjuvant treatment" refers to a treatment modifies the effect(s) of one or more other treatments (e.g., one or more pharmaceutical agents). For example, the delivery of one or more stimuli to the CA3 region of a patient's hippocampus may enhance the effectiveness of a pharmaceutical agent (by restoring the therapeutic efficacy of a drug to which the patient had previously become habituated, for example). In some embodiments, delivery of one or more stimuli to the patient's brain may reduce or eliminate the need for one or more treatments (e.g., one or more pharmaceutical agents).

As used herein, the term "and/or" includes any and all combinations of one or more of the associated listed items.

As used herein, the terms "comprise," "comprises," "comprising," "include", "includes" and "including" specify the presence of stated features, integers, steps, operations, elements, and/or components, but do not preclude the presence or addition of one or more other features, integers, steps, operations, elements, components, and/or groups thereof.

As used herein, the term "neuronal activity" refers to electrical impulses generated by one or more neurons. Thus, "detect neuronal activity" (and grammatical variants thereof) refers to the detection of electrical impulses generated by one or more neurons (using one or more implantable electrodes, for example).

As used herein, the term "patient" refers to both human subjects and animal subjects, including, but not limited to, mice, rats, rabbits, cats, dogs, pigs, horses, monkeys, apes, etc. The patient may be male or female. That patient may be of any suitable age, including infant, juvenile, adolescent, adult and geriatric ages. In some embodiments, the methods, devices and systems of the present invention may be used to induce physiological and/or psychological responses in a patient for medically diagnostic and/or therapeutic purposes. For example, the methods, devices and systems of the present invention may be used to diagnose and/or treat mammalian subjects, such as mice, rats, pigs and monkeys, for medical research or veterinary purposes.

As used herein, the term "seizure" refers to an abnormal electrical discharge in the brain and/or to the physical manifestations (e.g., sensory disturbances, convulsions, loss of consciousness) resulting from abnormal electrical discharges in the brain. In some embodiments, the seizure is an epileptic seizure. In some embodiments, the seizure is a mesial temporal lobe seizure.

As used herein, the terms "treatment," "treat," and "treating" refer to reversing, alleviating, reducing the severity of delaying the onset of, inhibiting the progress of or preventing a disease or disorder as described herein, or at least one symptom of a disease or disorder as described herein (e.g., inhibiting and/or preventing the propagation of a hippocampal seizure into one or more other areas of the brain). In some embodiments, treatment may be administered after one or more symptoms have developed (e.g., following the onset of one or more sensory disturbances). In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence. Treatment may be as an adjuvant treatment as further described herein.

The methods and devices of the present invention may be used to predict, prevent, detect and/or treat seizures (e.g., epileptic seizures).

Methods and devices of the present invention may be useful for predicting a seizure prior to its earliest inception. In some embodiments, the seizure is detected about 0.1 ms to about 30 minutes, about 0.1 ms to about 20 minutes, about 0.1 ms to about 10 minutes, about 0.1 ms to about 1 minute, about 0.1 ms to about 500 ms, about 500 ms to about 1 sec, about 1 to about 5 sec, about 5 to about 10 seconds, about 10 to about 30 seconds, about 30 sec to about 1 min or about 1 min to about 10 min prior to the onset of a seizure (e.g., prior to the onset of any sensory disturbance, alteration of consciousness and/or convulsion associated with a seizure). In some embodiments, the seizure may be predicted at least about 1, 2, 3, 4, 5, 6, 7, 8, 9, 10, 15, 20, 25, 30, 40, 50, 60, 70, 80, 90, 100, 125, 150, 175, 200, 250, 300, 350, 400, 450, 500, 550, 600, 650, 700, 750, 800, 850, 900, 950 ms or more prior to the onset of any sensory disturbance, alteration of consciousness and/or convulsion associated with a seizure. In some embodiments, the seizure may be predicted at least about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20 minutes or more prior to the onset of any sensory disturbance, alteration of consciousness and/or convulsion associated with a seizure.

Methods and devices of the present invention may be useful for detecting a seizure at any point during the life cycle of the seizure, including, but not limited to, the pre-ictal stage and the ictal stage. In some embodiments, the seizure may be detected in the absence of any sensory disturbances (e.g., prior to the onset of one or more sensory disturbances (i.e., in the pre-"aura" stage)). In some embodiments, the seizure may be detected following the onset of one or more sensory disturbances (i.e., during the "aura" stage). In some embodiments, the seizure may be detected in the absence of altered consciousness (e.g., prior to any alteration of consciousness). In some embodiments, the seizure may be detected in the absence of any convulsions (e.g., prior to the onset of one or more convulsions). In some embodiments, the seizure may be detected following the onset of one or more convulsions. In some embodiments, the seizure may be detected in the absence of a loss of consciousness (e.g., prior to a loss of consciousness).

Methods and devices of the present invention may be useful for predicting and/or detecting a seizure. In some embodiments, the seizure may be predicted and/or detected based upon neuronal activity in the perforant pathway, the hippocampal formation (e.g., in the hippocampus and/or the subiculum) and/or associated cortical regions (e.g., entorhinal cortex). In some embodiments, the seizure may be predicted and/or detected based upon neuronal activity in a patient's hippocampus (e.g., neuronal activity in the CA1, CA2, CA3 and/or Schaffer collateral region(s) of a patient's hippocampus). In some embodiments, the seizure may be predicted and/or detected using an algorithm (e.g., an algorithm that predicts neuronal activity in the CA1 region of the hippocampus based upon neuronal activity detected in the CA3 and/or the Schaffer collateral regions of the hippocampus).

Methods and devices of the present invention may be useful for inhibiting and/or preventing the propagation of a seizure in a patient's brain. In some embodiments, the seizure may be inhibited and/or prevented from propagating from one lobe of the brain to another (e.g., from the temporal lobe to the frontal lobe). In some embodiments, the seizure may be inhibited and/or prevented from propagating within a particular lobe (e.g., from the hippocampus to the subiculum, from the subiculum to entorhinal cortex, etc.). In some embodiments, the seizure may be inhibited and/or prevented from propagating from one region of the hippocampus to another (e.g., from the CA3 region to the CA1 region).

As noted above, present invention provides methods of predicting and/or detecting a seizure (e.g., a mesial temporal lobe seizure).

In some embodiments, the method comprises, consists essentially of or consists of detecting neuronal activity in one or more regions of a patient's brain (e.g., one or more regions of a patient's hippocampus) and analyzing the detected neuronal activity to predict and/or detect a seizure.

In some embodiments, the method comprises, consists essentially of or consists of detecting neuronal activity in the CA3 region of a patient's hippocampus and analyzing the detected neuronal activity to predict and/or detect a seizure.

In some embodiments, the method comprises, consists essentially of or consists of detecting neuronal activity in the CA3 region of a patient's hippocampus and at least one alternate region of the patient's brain and analyzing the detected neuronal activity to predict and/or detect a seizure. The at least one alternate region may comprise one or more of the following: the Schaffer collateral region of the hippocampus, the CA1 region of the hippocampus, the CA2 region of the hippocampus, the amygdala, the perforant pathway, the subiculum, the entorhinal cortex, a neocortical region (e.g., a neocortical region of the temporal, frontal, parietal or occipital lobe), the cerebellum and the cingulate cortex. Thus, in some embodiments, the method comprises, consists essentially of or consists of detecting neuronal activity in the CA3 and CA1 regions of a patient's hippocampus and analyzing the detected neuronal activity to predict and/or detect a seizure. Similarly, in some embodiments, the method comprises, consists essentially of or consists of detecting neuronal activity in the CA3 and Schaffer collateral regions of a patient's hippocampus and analyzing the detected neuronal activity to predict and/or detect a seizure.

In some embodiments, the method comprises, consists essentially of or consists of detecting neuronal activity in the Schaffer collateral region of a patient's hippocampus and analyzing the detected neuronal activity to predict and/or detect a seizure.

In some embodiments, the method comprises, consists essentially of or consists of detecting neuronal activity in the Schaffer collateral region of a patient's hippocampus and at least one alternate region of the patient's brain and analyzing the detected neuronal activity to predict and/or detect a seizure. The at least one alternate region may comprise one or more of the following: the CA3 region of the hippocampus, the CA1 region of the hippocampus, the CA2 region of the hippocampus, the amygdala, the perforant pathway, the subiculum, the entorhinal cortex and, a neocortical region (e.g., a neocortical region of the temporal, frontal, parietal or occipital lobe), the cerebellum and the cingulate cortex. Thus, in some embodiments, the method comprises, consists essentially of or consists of detecting neuronal activity in the Schaffer collateral and CA1 regions of a patient's hippocampus and analyzing the detected neuronal activity to predict and/or detect a seizure. Similarly, in some embodiments, the method comprises, consists essentially of or consists of detecting neuronal activity in the CA3 and Schaffer collateral regions of a patient's hippocampus and analyzing the detected neuronal activity to predict and/or detect a seizure.

In some embodiments, the method comprises, consists essentially of or consists of detecting neuronal activity in the CA1 region of a patient's hippocampus and analyzing the detected neuronal activity to predict and/or detect a seizure.

In some embodiments, the method comprises, consists essentially of or consists of detecting neuronal activity in the CA1 region of a patient's hippocampus and at least one alternate region of the patient's brain and analyzing the detected neuronal activity to predict and/or detect a seizure. The at least one alternate region may comprise one or more of the following: the CA3 region of the hippocampus, the Schaffer collateral region of the hippocampus, the CA2 region of the hippocampus, the amygdala, the perforant pathway, the subiculum, the entorhinal cortex, a neocortical region (e.g., a neocortical region of the temporal, frontal, parietal or occipital lobe), the cerebellum and the cingulate cortex. Thus, in some embodiments, the method comprises, consists essentially of or consists of detecting neuronal activity in the CA3 and CA1 regions of a patient's hippocampus and analyzing the detected neuronal activity to predict and/or detect a seizure. Similarly, in some embodiments, the method comprises, consists essentially of or consists of detecting neuronal activity in the CA1 and Schaffer collateral regions of a patient's hippocampus and analyzing the detected neuronal activity to predict and/or detect a seizure.

In some embodiments, the method comprises, consists essentially of or consists of detecting neuronal activity in the CA2 region of a patient's hippocampus and analyzing the detected neuronal activity to predict and/or detect a seizure.

In some embodiments, the method comprises, consists essentially of or consists of detecting neuronal activity in the CA2 region of a patient's hippocampus and at least one alternate region of the patient's brain and analyzing the detected neuronal activity to predict and/or detect a seizure. The at least one alternate region may comprise one or more of the following: the CA3 region of the hippocampus, the Schaffer collateral region of the hippocampus, the CA1 region of the hippocampus, the amygdala, the perforant pathway, the subiculum, the entorhinal cortex, a neocortical region (e.g., a neocortical region of the temporal, frontal, parietal or occipital lobe), the cerebellum and the cingulate cortex. Thus, in some embodiments, the method comprises, consists essentially of or consists of detecting neuronal activity in the CA3 and CA2 regions of a patient's hippocampus and analyzing the detected neuronal activity. Similarly, in some embodiments, the method comprises, consists essentially of or consists of detecting neuronal activity in the CA2 and Schaffer collateral regions of a patient's hippocampus and analyzing the detected neuronal activity to predict and/or detect a seizure. Likewise, in some embodiments, the method comprises, consists essentially of or consists of detecting neuronal activity in the CA2 region of a patient's hippocampus and at least one associated cortical region and analyzing the detected neuronal activity to predict and/or detect a seizure.

In some embodiments, the method comprises, consists essentially of or consists of detecting neuronal activity in a patient's perforant pathway and analyzing the detected neuronal activity to predict and/or detect a seizure.

In some embodiments, the method comprises, consists essentially of or consists of detecting neuronal activity in a patient's perforant pathway and at least one alternate region of the patient's brain and analyzing the detected neuronal activity to predict and/or detect a seizure. The at least one alternate region may comprise one or more of the following: the CA3 region of the hippocampus the Schaffer collateral region of the hippocampus, the CA1 region of the hippocampus, the CA2 region of the hippocampus, the amygdala, the subiculum, the entorhinal cortex, a neocortical region (e.g., a neocortical region of the temporal, frontal, parietal or occipital lobe), the cerebellum and the cingulate cortex. Thus, in some embodiments, the method comprises, consists essentially of or consists of detecting neuronal activity in a patient's perforant pathway and at least one region of the patient's hippocampus and analyzing the detected neuronal activity. Similarly, in some embodiments, the method comprises, consists essentially of or consists of detecting neuronal activity a patient's perforant pathway and the patient's subiculum and analyzing the detected neuronal activity to predict and/or detect a seizure. Likewise, in some embodiments, the method comprises, consists essentially of or consists of detecting neuronal activity in a patient's perforant pathway and the patient's entorhinal cortex and analyzing the detected neuronal activity to predict and/or detect a seizure.

In some embodiments, the method comprises, consists essentially of or consists of detecting neuronal activity in a patient's subiculum and analyzing the detected neuronal activity to predict and/or detect a seizure.

In some embodiments, the method comprises, consists essentially of or consists of detecting neuronal activity in a patient's subiculum and at least one alternate region of the patient's brain and analyzing the detected neuronal activity to predict and/or detect a seizure. The at least one alternate region may comprise one or more of the following: the CA3 region of the hippocampus the Schaffer collateral region of the hippocampus, the CA1 region of the hippocampus, the CA2 region of the hippocampus, the amygdala, the perforant pathway, the entorhinal cortex, a neocortical region (e.g., a neocortical region of the temporal, frontal, parietal or occipital lobe), the cerebellum and the cingulate cortex. Thus, in some embodiments, the method comprises, consists essentially of or consists of detecting neuronal activity in a patient's subiculum and at least one region of the patient's hippocampus and analyzing the detected neuronal activity. Similarly, in some embodiments, the method comprises, consists essentially of or consists of detecting neuronal activity a patient's subiculum and the patient's perforant pathway and analyzing the detected neuronal activity to predict and/or detect a seizure. Likewise, in some embodiments, the method comprises, consists essentially of or consists of detecting neuronal activity in a patient's subiculum and the patient's entorhinal cortex and analyzing the detected neuronal activity to predict and/or detect a seizure.

In some embodiments, the method comprises, consists essentially of or consists of detecting neuronal activity in a patient's entorhinal cortex and analyzing the detected neuronal activity to predict and/or detect a seizure.

In some embodiments, the method comprises, consists essentially of or consists of detecting neuronal activity in a patient's entorhinal cortex and at least one alternate region of the patient's brain and analyzing the detected neuronal activity to predict and/or detect a seizure. The at least one alternate region may comprise one or more of the following: the CA3 region of the hippocampus the Schaffer collateral region of the hippocampus, the CA1 region of the hippocampus, the CA2 region of the hippocampus, the amygdala, the perforant pathway, the subiculum, a neocortical region (e.g., a neocortical region of the temporal, frontal, parietal or occipital lobe), the cerebellum and the cingulate cortex. Thus, in some embodiments, the method comprises, consists essentially of or consists of detecting neuronal activity in a patient's entorhinal cortex and at least one region of the patient's hippocampus and analyzing the detected neuronal activity to predict and/or detect a seizure. Similarly, in some embodiments, the method comprises, consists essentially of or consists of detecting neuronal activity a patient's entorhinal cortex and the patient's perforant pathway and analyzing the detected neuronal activity. Likewise, in some embodiments, the method comprises, consists essentially of or consists of detecting neuronal activity in a patient's entorhinal cortex and the patient's subiculum and analyzing the detected neuronal activity to predict and/or detect a seizure.

Any suitable means may be used to detect neuronal activity, including, but not limited to, subdural electrodes and stereotactically-placed depth electrodes. In some embodiments, neuronal activity is detected using one or more single-unit neuron detectors (e.g., one or more microelectrodes) and/or one or more multi-unit neuron detectors (e.g., one or more macroelectrodes and/or one or more microelectrode arrays). In some embodiments, the method comprises, consists essentially of or consists of detecting neuronal activity in a patient's hippocampus (e.g., in the CA3, Schaffer collateral and/or CA1 regions of a patient's hippocampus) using one or more microelectrodes and/or one or more microelectrode arrays. Although seizure loci are conventionally localized at the multicellular field level using multiple depth electrodes positioned in the bilateral hippocampi, methods of the present invention may utilize electrodes with both microrecording capabilities and current recording capabilities, thereby allowing for the capture of single- and multi-unit neuronal ensemble patterns and the development of unique algorithmic models of the epileptic human brain and unique seizure prediction/detection models that are capable of predicting and/or detecting a seizure at earlier time points than previously established. For example, microelectrodes may be positioned in the CA3, Schaffer colatteral and/or CA1 regions of the hippocampus to detect single-unit neuronal ensemble discharges, whilst microelectrodes are used to detect neuronal discharges in the amygdala, hippocampus, perforant pathway, subiculum, entorhinal cortex and/or one or more neocortical regions, thereby allowing for the development of unique models for predicting and/or detecting mesial temporal lode seizures. Accordingly, methods of the present invention may be used to predict and/or detect seizures at earlier time points than previously known methods.

The detected neuronal activity may be analyzed using any suitable methods/devices, including, but not limited to, the methods/device describe herein and the methods/devices described in U.S. Pat. No. 7,460,904, Berger et al., J. NEURONAL ENG. 8:046017 (2011); Brown et al., NEURAL COMPUTATION 14:346 (2002); Granger, ECONOMETRICA 37:424 (1969); Hampson et al., IEEE TRANSACTIONS 20:184 (2012); Hampson et al., J. NEUROSCI METHODS 182:195 (2009); Song et al., NEURAL NETWORKS 22:1340 (2009); Zanos et al., IEEE TRANSACTIONS 16:336 (2008), the disclosure of each of which is incorporated herein by reference in its entirety.

Any suitable aspect of the neuronal activity may be analyzed, including, but not limited to, the waveform, frequency and rhythmicity of the neuronal activity. In some embodiments, the presence and/or absence of rhythmic unit bursting (e.g., rhythmic unit bursting that coincides with increases/decreases in local field potentials) in one or more regions of the patient's brain (e.g., one or more regions of the patient's hippocampus) may be analyzed. In some embodiments, the recruitment of neurons into one or more a rhythmic firing patterns may be analyzed. For example, in some embodiments, the analysis focuses on detecting the occurrence of rhythmical single- and/or multi-unit neuronal depolarization in one or more regions of the patient's brain (e.g., the CA3, Schaffer collateral and/or CA1 regions of the patient's hippocampus) that coincide spatiotemporally with local field potential increases and/or synchronize in discharge frequency.

In some embodiments, analyzing the detected neuronal activity to predict and/or detect a seizure comprises comparing the detected neuronal activity with neuronal activity detected prior to, during and/or following a previous seizure. For example, in an embodiment comprising the detection of neuronal activity in the CA3 region of a patient's hippocampus, analyzing the detected neuronal activity may comprise comparing the neuronal activity detected in the CA3 region of the patient's hippocampus with neuronal activity that was detected in the CA3 region of the patient's hippocampus prior to, during and/or following a previous seizure and/or with neuronal activity that was detected in the CA3 region(s) of one or more other patients prior to, during and/or following a seizure. Likewise, in an embodiment comprising the detection of neuronal activity in the CA3 and CA1 regions of a patient's hippocampus, analyzing the detected neuronal activity may comprise comparing the neuronal activity detected in the CA3 and CA1 regions of the patients hippocampus with neuronal activity that was detected in the CA3 and CA1 regions of the patient's hippocampus prior to, during and/or following a previous seizure and/or with neuronal activity that was detected in the CA3 and CA1 regions of one or more other patients prior to, during and/or following a seizure.

In some embodiments, analyzing the detected neuronal activity to predict and/or detect a seizure comprises comparing the detected neuronal activity with a neuronal activity signature associated with one or more types of seizure. For example, in an embodiment comprising the detection of neuronal activity in the CA3 region of a patient's hippocampus, analyzing the detected neuronal activity may comprise comparing the neuronal activity detected in the CA3 region of the patient's hippocampus with a neuronal activity signature derived by aggregating the neuronal activity detected in the CA3 regions of a plurality of patient's prior to and/or during a seizure (e.g., a mesial temporal lobe seizure). Likewise, in an embodiment comprising the detection of neuronal activity in the CA3 and CA1 regions of a patient's hippocampus, analyzing the detected neuronal activity may comprise comparing the neuronal activity detected in the CA3 and CA1 regions of the patient's hippocampus with a neuronal activity signature derived by aggregating the neuronal activity detected in the CA3 and CA1 regions of a plurality of patient's prior to and/or during a seizure (e.g., a mesial temporal lobe seizure).

In some embodiments, analyzing the detected neuronal activity to predict and/or detect a seizure comprises predicting future neuronal activity based upon the detected neuronal activity (e.g., predicting that the detected neuronal activity will cause and/or will be followed by abnormal electrical discharges). For example, in an embodiment comprising the detection of neuronal activity in the CA3 region of a patient's hippocampus, analyzing the detected neuronal activity may comprise predicting future neuronal activity in the CA3 region of the patient's hippocampus, the Schaffer collateral region of the patient's hippocampus, the CA1 region of the patient's hippocampus, in the patient's perforant pathway, in the patient's subiculum and/or in the patients entorhinal cortex based upon the neuronal activity detected in the CA3 region of the patient's hippocampus. Likewise, in an embodiment comprising the detection of neuronal activity in the CA3 and CA1 regions of a patient's hippocampus, analyzing the detected neuronal activity may comprise predicting future neuronal activity in the CA3 region of the patient's hippocampus, the Schaffer collateral region of the patient's hippocampus, the CA1 region of the patient's hippocampus, in the patient's perforant pathway, in the patient's subiculum and/or in the patient's entorhinal cortex based upon the neuronal activity detected in the CA3 and CA1 regions of the patient's hippocampus.

In some embodiments, predicting future neuronal activity based upon the detected neuronal activity comprises the use of a predictive algorithm. Any suitable algorithm may be used, including, but not limited to, nonlinear algorithms and multi-input multi-output algorithms. See, e.g., Berger at al., J. NEURONAL ENG. 8:046017 (2011); Hampson at al., IEEE TRANSACTIONS 20:184 (2012); Song at al., NEURAL NETWORKS 22:1340 (2009); Zanos et al., IEEE TRANSACTIONS 16:336 (2008). For example, in an embodiment comprising the detection of neuronal activity in the CA3 region of a patient's hippocampus, predicting future neuronal activity based upon the detected neuronal activity may comprise the use of a predictive algorithm that that predicts future neuronal activity in the CA3 region of the patient's hippocampus, the Schaffer collateral region of the patient's hippocampus, the CA1 region of the patient's hippocampus, in the patient's perforant pathway, in the patient's subiculum and/or in the patient's entorhinal cortex based upon the neuronal activity detected in the CA3 region of the patient's hippocampus. Likewise, in an embodiment comprising the detection of neuronal activity in the CA3 and CA1 regions of a patient's hippocampus, predicting future neuronal activity based upon the detected neuronal activity may comprise the use of a predictive algorithm that that predicts future neuronal activity in the CA3 region of the patient's hippocampus, the Schaffer collateral region of the patient's hippocampus, the CA1 region of the patient's hippocampus, in the patient's perforant pathway, in the patient's subiculum and/or in the patient's entorhinal cortex based upon the neuronal activity detected in the CA3 and CA1 regions of the patient's hippocampus.

As noted above, the present invention also provides methods useful for inhibiting and/or preventing the propagation of a seizure (e.g., a mesial temporal lobe seizure).

In some embodiments, the method comprises, consists essentially of or consists of predicting and/or detecting a seizure in a patient and delivering a stimulus to one or more regions of the patient's brain, thereby inhibiting and/or preventing propagation of the seizure.

Any suitable method/device may be used to predict and/or detect the seizure, including, but not limited to, the methods and devices described herein.

Any suitable stimulus may be delivered, including, but not limited to, electrical impulses.

A stimulus may be delivered to any suitable region of the patient's brain, including, but not limited to, the CA3 region of the hippocampus, the Schaffer collateral region of the hippocampus, the CA1 region of the hippocampus, the CA2 region of the hippocampus, the amygdala, the perforant pathway, the subiculum, the entorhinal cortex, the cerebellum, the cingulate cortex and neocortical regions, including, but not limited to, neocortical regions of the temporal, frontal, parietal and occipital lobes and/or any connections between two or more of the aforementioned regions. Thus, in some embodiments, the method comprises predicting and/or detecting a seizure in a patient and delivering one or more stimuli to the CA3 region of a patient's hippocampus, one or more stimuli to the Schaffer collateral region of the patient's hippocampus, one or more stimuli to the CA1 region of the patient's hippocampus, one or more stimuli to the CA2 region of the patient's hippocampus, one or more stimuli to the patient's perforant pathway, one or more stimuli to the patient's subiculum and/or one or more stimuli to the patient's entorhinal cortex.

Any suitable device may be used to carry out the aforementioned methods, including, but not limited to, the devices described hereinafter.

As noted above, the present invention also provides devices useful for predicting, preventing, detecting and/or treating a seizure (e.g., a mesial temporal lobe seizure).

In some embodiments, the device comprises, consists essentially of or consists of a controller that is operatively connected to one or more electrodes.

In some embodiments, the device comprises, consists essentially of or consists of a controller that is operatively connected to one or more electrodes configured to detect neuronal activity in the CA3 region of a patient's hippocampus, one or more electrodes configured to detect neuronal activity in the Schaffer collateral region of a patient's hippocampus, one or more electrodes configured to detect neuronal activity in the CA1 region of a patient's hippocampus, one or more electrodes configured to detect neuronal activity in the CA2 region of a patient's hippocampus, one or more electrodes configured to detect neuronal activity in a patient's perforant pathway, one or more electrodes configured to detect neuronal activity in a patient's subiculum, one or more electrodes configured to detect neuronal activity in a patient's entorhinal cortex and/or one or more electrodes configured to detect neuronal activity in a cortical area that is associated with one or more of the aforementioned regions/structures (e.g., a cortical area that receives input from one or more of the aforementioned regions/structures).

In some embodiments, the device comprises, consists essentially of or consists of a controller that is operatively connected to one or more electrodes configured to deliver one or more stimuli to the CA3 region of a patient's hippocampus, one or more electrodes configured to deliver one or more stimuli to the Schaffer collateral region of a patient's hippocampus, one or more electrodes configured to deliver one or more stimuli to the CA1 region of a patient's hippocampus, one or more electrodes configured to deliver one or more stimuli to the CA2 region of a patient's hippocampus, one or more electrodes configured to deliver one or more stimuli to a patient's perforant pathway, one or more electrodes configured to deliver one or more stimuli to a patient's subiculum, one or more electrodes configured to deliver one or more stimuli to a patient's entorhinal cortex and/or one or more electrodes configured to deliver one or more stimuli to a cortical area that is associated with one or more of the aforementioned regions/structures (e.g., a cortical area that receives input from one or more of the aforementioned regions/structures).

Devices of the present invention may comprise any suitable electrode(s), including, but not limited to, subdural electrodes and stereotactically-placed depth electrodes. In some embodiments, the device comprises one or more single-unit neuron detectors (e.g., one or more microelectrodes) and/or one or more multi-unit neuron detectors (e.g., one or more macroelectrodes and/or on or more microelectrode arrays). In some embodiments, the device comprises one or more electrodes with microrecording capability and current recording capability. Such electrodes may be used while collecting conventional clinical data for analysis of seizure generation and propagation across multiple spatiotemporal scales. Moreover, as noted above such electrodes may be used to capture single- and multi-unit neuronal ensemble patterns, which may themselves be used to develop unique algorithmic models of the epileptic human brain and unique seizure prediction models. Accordingly, devices of the present invention may be used to predict and/or detect seizures at earlier time points than previously known methods.

The electrode(s) may be configured so as to be insertable/implantable in any suitable location in a patient's brain, including, but not limited to, the hippocampal formation (e.g., dentate gyrus, hippocampus, subiculum), the perforant pathway, the entorhinal cortex and cortical areas associated with one or more of the aforementioned regions/structures (e.g., a cortical area that receives input from one or more of the aforementioned regions/structures). In some embodiments, the device comprises one or more electrodes configured so as to be insertable/implantable in a patient's hippocampus (e.g., into the CA1, CA2, CA3 and/or Schaffer collateral region(s) of a patient's hippocampus). In some embodiments, the device comprises one or more electrodes configured so as to be insertable/implantable in the CA3 region of a patient's hippocampus, one or more electrodes configured so as to be insertable/implantable in the Schaffer collateral region of a patient's hippocampus and/or one or more electrodes configured so as to be insertable/implantable in the CA1 region of a patient's hippocampus.

The electrode(s) may be configured to detect neuronal activity in any suitable location in a patient's brain, including, but not limited to, the hippocampal formation (e.g., dentate gyrus, hippocampus, subiculum), the perforant pathway the entorhinal cortex and cortical areas associated with one or more of the aforementioned regions/structures (e.g., a cortical area that receives input from one or more of the aforementioned regions/structures). In some embodiments, the device comprises one or more electrodes configured to detect neuronal activity in a patient's hippocampus (e.g., in the CA1, CA2, CA3 and/or Schaffer collateral region(s) of a patient's hippocampus). In some embodiments, the device comprises one or more electrodes configured to detect neuronal activity in the CA3 region of a patient's hippocampus, one or more electrodes configured to detect neuronal activity in the Schaffer collateral region of a patient's hippocampus and/or one or more electrodes configured to detect neuronal activity in the CA1 region of a patient's hippocampus.

The electrode(s) may be configured to transmit any suitable data to the controller, including, but not limited to, electrical signals corresponding to the detected neuronal activity. In some embodiments, the electrode(s) is/are configured to capture electrical impulses generated by one or more neurons and to transmit those electrical impulses to the controller.

The electrode(s) may be configured to deliver any suitable stimulus, including, but not limited to, electrical stimuli (e.g., one or more electrical pulses). In some embodiments, the device comprises one or more electrodes configured to deliver electrical stimuli that are of sufficient timing, pulse width, charge, frequency and/or intensity to disrupt seizure activity prior to and/or during propagation.

The electrode(s) may be configured to deliver one or more stimuli to any suitable location in a patient's brain, including, but not limited to, the hippocampal formation (e.g., dentate gyms, hippocampus, subiculum), the perforant pathway the entorhinal cortex and cortical areas associated with one or more of the aforementioned regions/structures (e.g., a cortical area that receives input from one or more of the aforementioned regions/structures). In some embodiments, the device comprises one or more electrodes configured to deliver a stimulus to a patient's hippocampus (e.g., to the CA1, CA2, CA3 and/or Schaffer collateral region(s) of a patient's hippocampus). In some embodiments, the device comprises one or more electrodes configured to deliver a stimulus to the patient's cerebellum, one or more electrodes configured to deliver a stimulus to the patient's perforant pathway, one or more electrodes configured to deliver a stimulus to the CA3 region of a patient's hippocampus, one or more electrodes configured to deliver a stimulus to the Schaffer collateral region of a patient's hippocampus, one or more electrodes configured to deliver a stimulus to the CA1 region of a patient's hippocampus, one or more electrodes configured to deliver a stimulus to the patient's subiculum and/or one or more electrodes configured to deliver a stimulus to the patient's entorhinal cortex.

Devices of the present invention may comprise any suitable controller, including, but not limited to, controllers configured so as to be implanted in and/or attached to a patient's body. For example, in some embodiments, the device may comprise a controller as described in U.S. Pat. No. 7,460,904, the disclosure of which is incorporated herein by reference in its entirety.

The controller may be operatively connected to the electrode(s) in any suitable manner. For example, the controller may be operatively connected to the electrode(s) via a detection lead and/or a stimulation lead. In those embodiments wherein the controller is operatively connected to a plurality of electrodes, the controller may be connected to each electrode separately (e.g., via a separate lead or set of leads). Individual leads and/or sets of leads may be bundled together to form one or more lead bundles. Leads, sets of leads and/or lead bundles may be operatively connected to the controller via a lead interface (e.g., an 18-pin connector).

The controller may be configured to receive data from any of the electrode(s) to which it is operatively connected. For example, the controller may be configured to receive data from one or more electrodes inserted/implanted in the perforant pathway, one or more electrodes inserted/implanted in the hippocampal formation (e.g., in the hippocampus and/or the subiculum), one or more electrodes inserted/implanted in the entorhinal cortex and/or one or more electrodes inserted/implanted in a cortical area associated with one or more of the aforementioned regions/structures (e.g., a cortical area that receives input from one or more of the aforementioned regions/structures). In some embodiments, the controller is configured to receive data from one or more electrodes inserted/implanted in the CA3 region of a patient's hippocampus, one or more electrodes inserted/implanted in the Schaffer collateral region of a patient's hippocampus and/or one or more electrodes inserted/implanted in the CA1 region of a patient's hippocampus.

The controller may be configured to receive any suitable data from the electrode(s) to which it is operatively connected, including, but not limited to, electrical signals corresponding to the neuronal activity detected by the electrode (s). In some embodiments, the controller is configured to receive electrical impulses captured by the electrode(s).

The controller may be configured to perform any suitable analysis responsive to receiving data from one or more electrodes, including, but not limited to, predicting whether/when a seizure will occur, predicting the severity of a seizure, predicting the duration of a seizure, detecting the onset of a seizure, detecting an ongoing seizure and/or detecting the cessation of a seizure. In some embodiments, the controller is configured to analyze data associated with neuronal activity using a predictive algorithm. See, e.g., Berger et al., J. NEURONAL ENG. 8:046017 (2011); Granger, ECONOMETRICA 37:424 (1969); Hampson et al., IEEE TRANSACTIONS 20:184 (2012); Song et al., NEURAL NETWORKS 22:1340 (2009); Zanos et al., IEEE TRANSACTIONS 16:336 (2008). In some embodiments, the controller is configured to analyze data associated with neuronal activity using an algorithm that predicts neuronal activity in the CA1 region of the hippocampus, the subiculum and/or the entorhinal cortex based upon neuronal activity detected in the CA3 and/or the Schaffer collateral regions of the hippocampus. In some embodiments, the controller is configured to analyze data associated with neuronal activity using an algorithm that predicts neuronal activity in cortical areas associated with the hippocampus formation based upon neuronal activity detected in the CA3, Schaffer collateral and/or CA1 regions of the hippocampus.

The controller may be configured to activate any of the electrode(s) to which it is operatively connected. For example, the controller may be configured to activate one or more electrodes inserted/implanted in the perforant pathway, one or more electrodes inserted/implanted in the hippocampal formation (e.g., in the hippocampus and/or the subiculum), one or more electrodes inserted/implanted the entorhinal cortex and/or one or more electrodes inserted/implanted in a cortical area associated with one or more of the aforementioned regions/structures (e.g., a cortical area that receives input from one or more of the aforementioned regions/structures). In some embodiments, the controller is configured to activate at least one electrode inserted/implanted in the patient's perforant pathway, at least one electrode inserted/implanted in the CA3 region of a patient's hippocampus, at least one electrode inserted/implanted in the Schaffer collateral region of a patient's hippocampus, at least one electrode inserted/implanted in the CA1 region of a patient's hippocampus, at least one electrode inserted/implanted in the patient's subiculum and/or at least one electrode inserted/implanted in the patient's entorhinal cortex.

The controller may be configured to activate one or more electrodes in response to any suitable trigger, including, but not limited to, detection of a seizure. For example, the controller may be configured to activate one or more electrodes responsive to predicting that a seizure is likely/imminent and/or predicting that activation of one or more electrodes may prevent the propagation of a seizure. In some embodiments, the controller is configured to activate one or more electrodes responsive to detecting a seizure in the patient's hippocampus (e.g., in the CA3, Schaffer collateral and/or CA1 regions of the hippocampus).

The controller may be configured to activate electrodes in any suitable manner. For example, the controller may be configured to activate an electrode such that the electrode delivers an electrical stimulus to a patient's brain (e.g., an electrical pulse). In some embodiments, the controller is configured to activate one or more electrodes to produce an electrical stimulus that inhibits and/or prevents the propagation of a seizure from one lobe of the brain to another (e.g., from the temporal lobe to the frontal lobe). In some embodiments, the controller is configured to activate one or more electrodes to produce an electrical stimulus that inhibits and/or prevents the propagation of a seizure within a particular lobe (e.g., from the hippocampus to the subiculum, from the subiculum to entorhinal cortex, etc.). In some embodiments, the controller is configured to activate one or more electrodes to produce an electrical stimulus that inhibits and/or prevents the propagation of a seizure from one region of the hippocampus to another (e.g., from the CA3 region to the CA1 region).

The controller may be configured to receive and/or transmit data over any suitable wired or wireless communications channel, including, but not limited to, a LAN, the Internet, a public telephone switching network, Bluetooth, WLAN and the like.

In some embodiments, the controller comprises memory, a processor and a power supply. As will be appreciated by one of skill in the art, the processor may be any commercially available or custom microprocessor. Memory can include, but is not limited to, the following types of devices: cache, ROM, PROM, EPROM, EEPROM, flash memory, SRAM and DRAM. The power supply may be an internal power supply (e.g., one or more rechargeable batteries that may be recharged without first being removed from the controller).

The controller's memory may comprise any suitable software and/or data, including, but not limited to, an operating system, applications, data and input/output (I/O) drivers.

As will be appreciated by one of skill in the art, the controller may use any suitable operating system, including, but not limited to, OS/2, AIX, OS/390 or System390 from International Business Machines Corp. (Armonk, N.Y.), Window CE, Windows NT, Windows95, Windows98, Windows2000, Windows 7 or Windows Vista from Microsoft Corp. (Redmond, Wash.), Mac OS from Apple, Inc. (Cupertino, Calif.), Unix, Linux or Android.

As will be appreciated by one of skill in the art, the controller may comprise any suitable application, including, but not limited to, one or more programs configured to implement one or more of the various features of the present invention.

For example, the controller may comprise a detection module configured to receive data associated with the detection of neuronal activity in one or more regions of a patient's brain; a prediction module configured to analyze data associated with the detection of neuronal activity in one or more regions of a patient's brain; an activation module configured to activate one or more electrodes; a network module configured to receive and/or transmit data and/or a safety module configured to deactivate the controller in the event of a system malfunction and/or failure. In some embodiments, two or more of the aforementioned modules are combined to form a single module configured to carry out the function(s) of each of the individual modules (e.g., the controller may comprise a detection-prediction module configured to receive and analyze data associated with the detection of neuronal activity in one or more regions of a patient's brain). In some embodiments, one of the aforementioned modules is split into two or more distinct modules. In some embodiments, one or more of the functions described below with respect to one of the modules described below is performed by one of the other modules described below.

Detection Module

In some embodiments, the controller comprises a detection module configured to receive and/or transmit data associated with the detection of neuronal activity in one or more regions of a patient's brain.

The detection module may be configured to receive and/or transmit data from/to any suitable device/module/database, including, but not limited to, one or more electrodes, other modules residing in the controller and databases residing in the controller. In some embodiments, the detection module is configured to receive data from one or more electrodes inserted/implanted in a patient's hippocampus (e.g., in the CA3, Schaffer collateral and/or CA1 regions of the patient's hippocampus), from one or more electrodes inserted/implanted in a patient's perforant pathway, from one or more electrodes inserted/implanted in a patient's subiculum, from one or more electrodes inserted/implanted in a patient's entorhinal cortex, from one or more electrodes inserted/implanted in a patient's cingulate cortex, from one or more electrodes inserted/implanted in a patient's cerebellum, from one or more electrodes inserted/implanted in a patient's neocortex (e.g., one or more electrodes inserted/implanted in a neocortical region of the patient's temporal, frontal, parietal and/or occipital lobes) and/or from a detection database residing in the controller. In some embodiments, the detection module is configured to transmit data to a detection database residing in the controller and/or to a prediction module residing in the controller.

The detection module may be configured to receive and/or transmit any suitable data, including, but not limited to, electrical signals captured by one or more electrodes inserted/implanted in a patient's brain. In some embodiments, the detection module is configured to receive and/or transmit electrical signals captured by one or more electrodes inserted/implanted in the one or more regions of a patient's hippocampus (e.g., the CA3, Schaffer collateral and/or CA1 regions of the patient's hippocampus).

Prediction Module

In some embodiments, the controller comprises a prediction module configured to analyze data associated with the detection of neuronal activity in one or more regions of a patient's brain.

The prediction module may be configured to receive and/or transmit data from/to any suitable device/module/database, including, but not limited to, other modules residing in the controller and databases residing in the controller. In some embodiments, the prediction module is configured to receive data from a detection module residing in the controller and/or from a detection database residing in the controller. In some embodiments, the prediction module is configured to transmit data to a prediction database residing in the controller and/or to an activation module residing in the controller.

The prediction module may be configured to receive, transmit and/or analyze any suitable data, including, but not limited to, data associated with the detection of neuronal activity in one or more regions of a patient's brain and data associated with its own analysis. In some embodiments, the prediction module is configured to receive and analyze data associated with the detection of neuronal activity in one or more regions of a patient's hippocampus (e.g., the CA3, Schaffer collateral and/or CA1 regions of the patient's hippocampus), one or more regions of a patient's perforant pathway, one or more regions of a patient's subiculum, one or more regions of a patient's entorhinal, one or more regions of a patient's cerebellum, one or more regions of a patient's cingulate cortex and/or one or more regions of a patient's neocortex (e.g., one or more regions of the patient's temporal, frontal, parietal and/or occipital lobes).

The prediction module may be configured to analyze electrical signals in any suitable manner. In some embodiments, the prediction module is configured to analyze data associated with neuronal activity using a predictive algorithm. See, e.g., Berger et al., J. NEURONAL ENG. 8:046017 (2011); Granger, ECONOMETRICA 37:424 (1969); Hampson et al., IEEE TRANSACTIONS 20:184 (2012); Song et al., NEURAL NETWORKS 22:1340 (2009); Zanos et al., IEEE TRANSACTIONS 16:336 (2008). In some embodiments, the prediction module is configured to analyze data associated with neuronal activity using an algorithm that predicts neuronal activity in the CA1 region of the hippocampus, the perforant pathway, the subiculum, the entorhinal cortex and/or one or more neocortical regions (e.g., a neocortical region of the temporal, frontal, parietal or occipital lobe) based upon neuronal activity detected in the CA3 and/or the Schaffer collateral regions of the hippocampus, in the cingulate cortex, in the cerebellum, etc. In some embodiments, the prediction module is configured to analyze data associated with neuronal activity using an algorithm that predicts neuronal activity in cortical areas associated with the hippocampus formation based upon neuronal activity detected in the CA3, Schaffer collateral and/or CA1 regions of the hippocampus. In some embodiments, the prediction module is configured to predict whether/when a seizure will occur, to predict the severity of a seizure, to predict the duration of a seizure, to detect the onset of a seizure, to detect an ongoing seizure and/or to detect the cessation of a seizure.

Activation Module

In some embodiments, the controller comprises an activation module configured to activate one or more electrodes (i.e., to control the magnitude, duration and other attributes of stimulation delivered by the electrode(s)).

The activation module may be configured to receive and/or transmit data from/to any suitable device/module/database, including, but not limited to, other modules residing in the controller and databases residing in the controller. In some embodiments, the activation module is configured to receive data from a prediction module residing in the controller and/or from an instruction database residing in the controller.

The activation module may be configured to receive and/or transmit any suitable data, including, but not limited to, instructions for activating one or more electrodes. In some embodiments, the activation module is configured to receive instructions for activating one or more electrodes inserted/implanted in a patient's hippocampus (e.g., in the CA3, Schaffer collateral and/or CA1 regions of the patient's hippocampus), one or more electrodes inserted/implanted in a patient's perforant pathway, one or more electrodes inserted/implanted in a patient's subiculum, one or more electrodes inserted/implanted in a patients entorhinal cortex, one or more electrodes inserted/implanted in a patient's cingulate cortex, one or more electrodes inserted/implanted in a patient's cerebellum and/or one or more electrodes inserted/implanted in a patients neocortex (e.g., one or more electrodes inserted/implanted in a neocortical regions of the patient's temporal, frontal, parietal and/or occipital cortex).

The activation module may be configured to activate the electrode(s) to deliver any suitable stimulus, including, but not limited to, one or more electrical impulses. In some embodiments, the activation module is configured to selectively and separately activate a plurality of electrodes (e.g., by activating only one of said plurality of electrodes, by sequentially activating the electrodes, by activating different electrodes using different stimulus parameters, combinations of some or all of the foregoing, etc.). In some embodiments, the activation module is configured to activate the electrode(s) responsive to a trigger. For example, the activation module may be configured to activate one or more electrodes if/when a seizure is predicted and/or detected (by a prediction module residing in the controller, for example). In some embodiments, the activation module is configured to adjust one or more attributes of electrode activation (e.g., magnitude, duration, etc.) in response to feedback received from one or more electrodes and/or one or more sensors.

Network Module

In some embodiments, the controller comprises a network module configured to receive, retrieve and/or transmit data.

The network module may be configured to receive, retrieve and/or transmit data from/to any suitable device/module/database, including, but not limited to, other modules residing in the controller and databases residing in the controller. In some embodiments, the network module is configured to receive data from a detection module residing in the controller, from a detection database residing in the controller, from a prediction module residing in the controller, from a prediction module residing in the controller and/or from an instruction database residing in the controller. In some embodiments, the network module is configured to transmit data to a detection database residing in the controller, to a prediction module residing in the controller, to a prediction module residing in the controller, to an instruction database residing in the controller and/or to an activation module residing in the controller.

The network module may be configured to receive, retrieve and/or transmit any suitable data, including, but not limited to, data associated with the detection of neuronal activity in one or more regions of a patient's brain, data associated with the analysis of data associated with the detection of neuronal activity in one or more regions of a patient's brain, data associated with one or more predicted/detected seizures and instructions for activating one or more electrodes. In some embodiments, the network module is configured to receive and/or retrieve data associated with the detection of neuronal activity in one or more regions of a patient's brain from a detection module/database residing in the controller. In some embodiments, the network module is configured to receive and/or retrieve data associated with one or more predicted/detected seizures from a prediction module/database residing in the controller. In some embodiments, the network module is configured to receive and/or retrieve instructions for activating one or more electrodes from a prediction module/database residing in the controller and/or from an instructions database. In some embodiments, the network module is configured to transmit data associated with the detection of neuronal activity in one or more regions of a patient's brain to a detection database residing in the controller and/or to prediction module residing in the controller. In some embodiments, the network module is configured to transmit data associated with one or more predicted/detected seizures to a prediction database residing in the controller and/or to an activation module residing in the controller. In some embodiments, the network module is configured to transmit instructions for activating one or more electrodes to an instructions database residing in the controller and/or to an activation module residing in the controller.

Safety Module

In some embodiments, the controller comprises a safety module configured to deactivate the controller in the event of a system malfunction and/or failure.

The safety module may be configured to deactivate the controller for any suitable reason, including, but not limited to, a malfunctioning electrode, overheating and faulty activation of one or more electrodes by the controller. In some embodiments, the safety module is configured to deactivate the controller if/when the temperature of an electrode surpasses a specified safety threshold. In some embodiments, the safety module is configured to deactivate the controller if/when the temperature of the controller surpasses a specified safety threshold. In some embodiments, the safety module is configured to deactivate the controller if/when one or more of the activation signals sent from the controller to the associated electrode(s) indicates that the system may be operating outside of a predefined safety range. For example, the safety module may be configured to deactivate the controller if/when an activation signal sent from the controller to an associated electrode exceeds the level of activation that would normally be required to deliver the necessary stimulus in a properly functioning system.

As will be appreciated by one of skill in the art, the controller may comprise any suitable data, including, but not limited to, static and/or dynamic data used by the operating system, applications, I/O device drivers and other software components, data associated with the detection of neuronal activity in one or more regions of a patient's brain and instructions for activating one or more electrodes. For example, the controller may comprise a detection database comprising data associated with the detection of neuronal activity in one or more regions of a patient's brain, a prediction database comprising data associated with one or more predicted/detected seizures and/or an instruction database comprising instructions for activating one or more electrodes. In some embodiments, two or more of the aforementioned databases are combined to form a single database comprising data from each of the individual databases (e.g., the controller may comprise a prediction-instruction database comprising data associated with one or more predicted/detected seizures and instructions for activating one or more electrodes). In some embodiments, one of the aforementioned databases is split into two or more distinct databases. In some embodiments, one or more of the data types described below with respect to one of the databases described below is stored in one of the other databases described below. The controller may be configured to transmit, receive and store data in a manner that ensures compliance with any and all applicable laws and/or regulations (e.g., the Health Insurance Portability and Accountability Act of 1996 (P.L. 104-191; "HIPAA")).

Detection Database

In some embodiments, the controller comprises a detection database configured to receive, store and/or transmit data associated with the detection of neuronal activity in one or more regions of a patient's brain (e.g, electrical signals captured by one or more electrodes inserted/implanted in the patient's brain).

The detection database may comprise any suitable type of memory including, but not limited to, cache, ROM, PROM, EPROM, EEPROM, flash memory, SRAM and DRAM.

The detection database may be configured to receive and/or transmit data from/to any suitable device/module/database, including, but not limited to, one or more electrodes and modules residing in the controller. In some embodiments, the detection database is configured to receive data from one or more electrodes implanted in a patient's hippocampus (e.g., in the CA3, Schaffer collateral and/or CA1 regions of the patient's hippocampus), from one or more electrodes implanted in a patient's perforant pathway, from one or more electrodes implanted in a patient's cingulate cortex, from one or more electrodes implanted in a patient's cerebellum, from one or more electrodes implanted in a patient's amygdalae, from one or more electrodes implanted in a patient's subiculum, from one or more electrodes implanted in a patient's entorhinal cortex, from one or more electrodes implanted in a patient's neocortex (e.g., in one or more neocortical regions of the patient's temporal, frontal, parietal and/or occipital lobes), from a detection module residing in the controller and/or from a prediction module residing in the controller. In some embodiments, the detection database is configured to transmit data to a detection module residing in the controller, to a prediction module residing in the controller and/or to an activation module residing in the controller.

Prediction Database

In some embodiments, the controller comprises a prediction database configured to receive, store and/or transmit data associated with the detection of neuronal activity in one or more regions of a patient's brain, data associated with the analysis of data associated with the detection of neuronal activity in one or more regions of a patient's brain and/or data associated with one or more predicted/detected seizures.

The prediction database may comprise any suitable type of memory including, but not limited to, cache, ROM, PROM, EPROM, EEPROM, flash memory, SRAM and DRAM.

The prediction database may be configured to receive and/or transmit data from/to any suitable device/module/database, including, but not limited to, modules residing in the controller. In some embodiments, the prediction database is configured to receive data from a detection module residing in the controller and/or from a detection database residing in the controller. In some embodiments, the prediction database is configured to transmit data to a prediction module residing in the controller.

Instruction Database

In some embodiments, the controller comprises an instruction database configured to receive, store and/or transmit instructions for activating one or more electrodes (e.g, electrical signals captured by one or more electrodes inserted/implanted in the patient's brain).

The instruction database may comprise any suitable type of memory including, but not limited to, cache, ROM, PROM, EPROM, EEPROM, flash memory, SRAM and DRAM.

The instruction database may be configured to receive and/or transmit data from/to any suitable device/module/database, including, but not limited to, modules residing in the controller. In some embodiments, the instruction database is configured to receive data from a prediction module residing in the controller. In some embodiments, the instruction database is configured to transmit data to an activation module residing in the controller.

Figure 1:
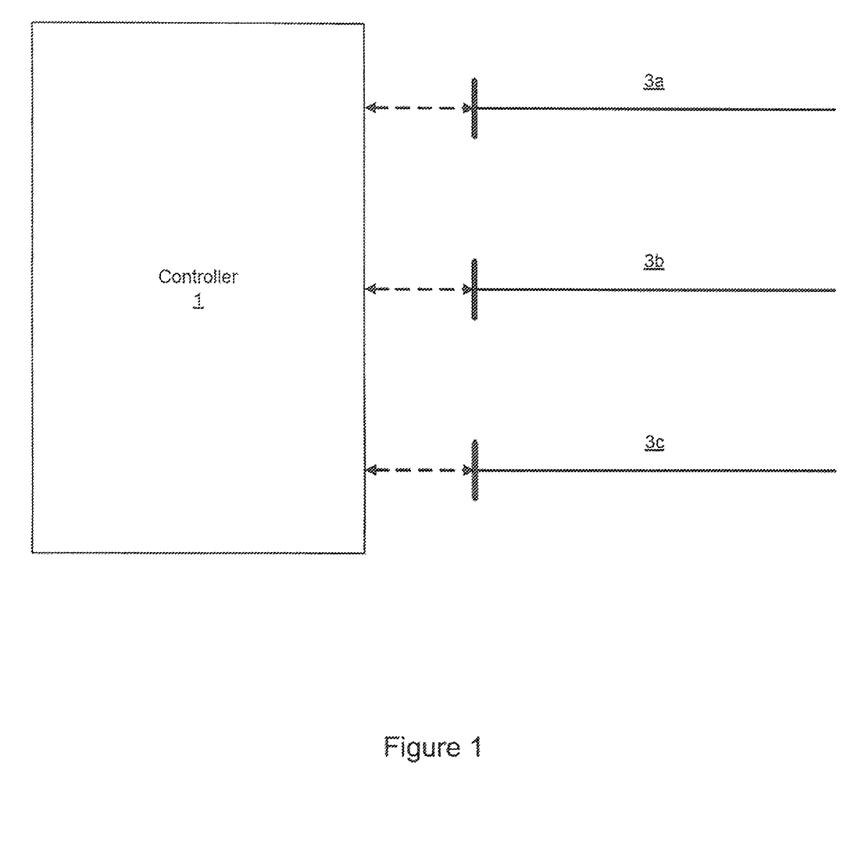
FIG. 1 is a block diagram of a device according to some embodiments of the present invention.

As shown in FIG. 1, in some embodiments, devices of the present invention comprise a controller 1 operatively connected to one or more electrodes 3a, 3b, 3c.

Figure 2:
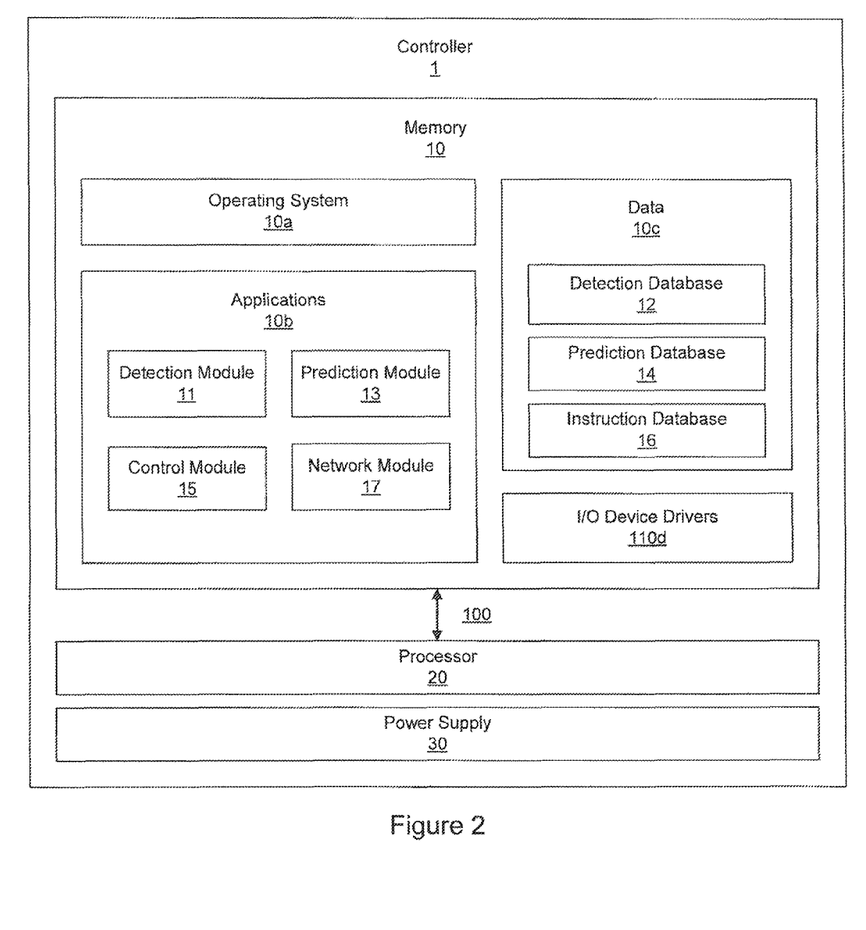
FIG. 2 is a block diagram of a controller according to some embodiments of the present invention.

As shown in FIG. 2, in some embodiments, the controller 1 comprises memory 10, a processor 20 and a power supply 30 (e.g., an internal power supply), wherein memory 10 is representative of the overall hierarchy of memory devices containing software and data used to implement the functionality of the controller 1 and wherein the processor 20 communicates with the memory 10 via an address/data bus 100. In particular embodiments, memory 10 comprises an operating system 10a, applications 10b (e.g., a detection module 11 configured to receive data associated with the detection of neuronal activity in one or more regions of a patient's brain; a prediction module 13 configured to analyze data associated with the detection of neuronal activity in one or more regions of a patient's brain; an activation module 15 configured to activate one or more electrodes and/or a network module 17 configured to receive and/or transmit data), data 10c (e.g., a detection database 12 comprising data associated with data associated with the detection of neuronal activity in one or more regions of a patient's brain; a prediction database 14 comprising data associated with one or more predicted/detected seizures and/or an instruction database 16 comprising instructions for activating one or more electrodes) and I/O drivers 10d.

The foregoing is illustrative of the present invention, and is not to be construed as limiting thereof. The invention is defined by the following claims, with equivalents of the claims to be included herein.

That which is claimed:

1. A method, comprising:
   detecting neuronal activity in the CA3 region of a patient's hippocampus;
   analyzing the detected neuronal activity to predict a seizure; and
   administering treatment in response to the step of analyzing the detected neuronal activity,
   wherein said analyzing step comprises comparing the detected neuronal activity with neuronal activity that was detected in the CA3 region of the patient's hippocampus and/or an at least one alternate region prior to and/or during a previous seizure.

2. The method of claim 1, further comprising:
   detecting neuronal activity in at least one alternate region of the patient's brain.

3. The method of claim 2, wherein, said at least one alternate region of the patient's brain comprises one or more regions selected from the group consisting of the Schaffer collateral region of the hippocampus, the CA1 region of the hippocampus, the CA2 region of the hippocampus, the perforant pathway, the subiculum, the entorhinal cortex and neocortical regions.

4. The method of claim 1, wherein said detecting step comprises using one or more electrodes to detect electrical impulses generated by one or more neurons.

5. The method of claim 1, wherein said detecting step comprises detecting electrical impulses using one or more electrodes configured to detect electrical impulses generated by a single neuron.

6. The method of claim 1, wherein said detecting step comprises detecting electrical impulses using one or more electrodes configured to detect electrical impulses generated by a plurality of neurons.

7. The method claim 1, wherein said analyzing step comprises predicting future neuronal activity based upon the detected neuronal activity.

8. The method of claim 7, wherein predicting future neuronal activity based upon the detected neuronal activity comprises the use off predictive algorithm.

9. The method of claim 1, wherein said analyzing step comprises comparing the detected neuronal activity with neuronal activity that was detected in the CA3 region and/or the at least one alternate region of one or more others patients prior to and/or during a seizure.

10. The method of claim 1, wherein said analyzing step comprises comparing the detected neuronal activity with a neuronal activity signature associated with one or more types of seizure.

11. The method of claim 1, wherein said analyzing step comprises analyzing the detected neuronal activity, using a computer program product comprising computer-readable code embodied in a computer-readable non-transient storage medium.

12. A method, comprising:
   predicting a seizure in a patient; and
   delivering a stimulus to one or more regions of the patient's brain to inhibit and/or prevent the propagation of the seizure, wherein said predicting and/or detecting step comprises the method of claim 1.

13. The method of claim 12, wherein a stimulus is delivered to one or more regions selected from the group consisting of the CA3 region of the hippocampus, the Schaffer collateral region of the hippocampus, the CA1 region of the hippocampus, the CA2 region of the hippocampus, the perforant pathway, the subiculum, the entorhinal cortex, the cerebellum and neocortical regions.

14. The method of claim 12, wherein delivering a stimulus to one or more regions of the patient's brain to inhibit and/or prevent the propagation of the seizure comprises delivering one or more electrical impulses to each of the stimulated regions.

15. The method of any claim 12, wherein said predicting and/or detecting step comprises analyzing neuronal activity using a computer program product comprising computer-readable code embodied in a computer-readable non-transient storage, medium.

16. The method of claim 12, wherein said delivering step comprises using one or more electrodes to deliver one or more electrical impulses to the patient's brain.

17. A device comprising:
a controller operatively connected to one or more electrodes,
wherein at least one of said one or more electrodes is configured to, detect neuronal activity in the CA3 region of a patient's hippocampus, and
wherein said controller is configured to predict a seizure based upon the neuronal activity detected in the CA3 region of a patient's hippocampus and a comparison of the detected neuronal activity with the neuronal activity that was detected in the CA3 region of the patient's hippocampus prior to and/or during a previous seizure,
wherein at least one of said one or more electrodes is configured to deliver an electrical stimulus to a region of the patient's hippocampus, and
wherein said controller is further configured to activate one or more of the electrodes configured to deliver an electrical stimulus to the region of the patient's hippocampus responsive to predicting and/or detecting the seizure.

18. The device of claim 17, wherein the region of the patient's hippocampus comprises the CA3 region.

19. The device of claim 18, wherein activation of said one or more of the electrodes configured to deliver an electrical stimulus to the CA3 region of the patient's hippocampus inhibits and/or prevents propagation of the seizure.

20. The device of claim 17, wherein said controller is configured to predict future neuronal activity based upon the detected neuronal activity.

21. The device of claim 20, wherein said controller is configured to predict future neuronal activity based upon the detected neuronal activity using of a predictive algorithm.

22. The device of claim 17, wherein said controller is configured to compare the detected neuronal activity with neuronal activity that was detected in the CA3 region and/or the at least one alternate region of one or more others patients prior to and/or during a seizure.

23. The device of claim 17, wherein said controller is configured to compare the detected neuronal activity with a neuronal activity signature associated with one or more types of seizure.

24. A device comprising:
a controller operatively connected to a plurality of electrodes,
wherein one or more of said plurality of electrodes is configured to detect neuronal activity in the CA3 region of a patient's hippocampus,
wherein one or more of said plurality of electrodes is configured to detect neuronal activity in an alternate region of the patient's brain, and
wherein said controller is configured to predict a seizure based upon the neuronal activity detected in the CA3 region of a patients hippocampus and the alternate region of the patient's brain and a comparison of the detected neuronal activity with the neuronal activity that was detected in the CA3 region of the patient's hippocampus and/or the at least one alternate region prior to and/or during a previous seizure, wherein one or more of said plurality of electrodes is configured to deliver an electrical stimulus to a region of the patient's hippocampus, and
wherein said controller is further configured to activate one or more of the electrodes configured to deliver an electrical stimulus to the region of the patient's hippocampus responsive to predicting and/or detecting the seizure.

25. The device of claim 24, wherein the region of the patient's hippocampus comprises the CA3 region.

26. The device of claim 24, wherein one or more of said plurality of electrodes is configured to deliver an electrical stimulus to the alternate region of the patient's brain, and
wherein said controller is further configured to activate one or more of the electrodes configured to deliver an electrical stimulus to the alternate region of the patient's brain responsive to predicting and/or detecting the seizure.

27. The device of claim 26, wherein activation of said one or more of the electrodes configured to deliver an electrical stimulus to the alternate region of the patient's brain inhibits and/or prevents propagation of the seizure.

28. The device of claim 24, wherein said alternate region of the patient's brain comprises the Schaffer collateral region of the patient's hippocampus, the CA1 region of the hippocampus, the CA2 region of the hippocampus, the perforant pathway, the subiculum, the entorhinal cortex, the cerebellum and/or neocortical regions.

* * * * *

UNITED STATES PATENT AND TRADEMARK OFFICE
CERTIFICATE OF CORRECTION

PATENT NO. : 10,123,750 B2  
APPLICATION NO. : 14/759092  
DATED : November 13, 2018  
INVENTOR(S) : Witcher et al.

Page 1 of 1

It is certified that error appears in the above-identified patent and that said Letters Patent is hereby corrected as shown below:

In the Claims

Column 26, Claim 8, Line 35: Please correct "off" to read -- of a --

Column 26, Claim 9, Line 39: Please correct "others" to read -- other --

Column 27, Claim 17, Line 12: Please correct "to," to read -- to --

Column 27, Claim 22, Line 43: Please correct "others" to read -- other --

Column 28, Claim 24, Line 12: Please correct "patients" to read -- patient's --

Signed and Sealed this  
Second Day of July, 2019

Andrei Iancu  
*Director of the United States Patent and Trademark Office*